(12) United States Patent
Zlokovic et al.

(10) Patent No.: US 8,778,985 B2
(45) Date of Patent: Jul. 15, 2014

(54) INHIBITING AMYLOID-BETA PEPTIDE/RAGE INTERACTION AT THE BLOOD-BRAIN BARRIER

(75) Inventors: Berislav V. Zlokovic, Rochester, NY (US); Rashid Deane, Rochester, NY (US); Benjamin L. Miller, Penfield, NY (US)

(73) Assignee: The University of Rochester, Rochester, NY (US)

( * ) Notice: Subject to any disclaimer, the term of this patent is extended or adjusted under 35 U.S.C. 154(b) by 1404 days.

(21) Appl. No.: 12/223,276

(22) PCT Filed: Jan. 26, 2007

(86) PCT No.: PCT/US2007/002220
§ 371 (c)(1),
(2), (4) Date: Jul. 25, 2008

(87) PCT Pub. No.: WO2007/089616
PCT Pub. Date: Aug. 9, 2007

(65) Prior Publication Data
US 2011/0039908 A1 Feb. 17, 2011

Related U.S. Application Data

(60) Provisional application No. 60/762,117, filed on Jan. 26, 2006.

(51) Int. Cl.
| | |
|---|---|
| A61K 31/404 | (2006.01) |
| C07D 209/14 | (2006.01) |
| A61K 31/40 | (2006.01) |
| C07D 207/335 | (2006.01) |
| A61K 31/167 | (2006.01) |
| C07C 235/84 | (2006.01) |
| A61K 31/166 | (2006.01) |
| C07C 233/64 | (2006.01) |
| A61P 25/28 | (2006.01) |

(52) U.S. Cl.
USPC ........... 514/415; 514/427; 514/616; 514/617; 548/504; 548/561; 564/155; 564/184

(58) Field of Classification Search
USPC .......... 514/415, 427, 616, 617; 548/504, 561; 564/155, 184
See application file for complete search history.

(56) References Cited

U.S. PATENT DOCUMENTS

| | | | |
|---|---|---|---|
| 4,725,581 A | | 2/1988 | Vincent et al. |
| 7,262,208 B2 * | | 8/2007 | Tucker et al. ............... 514/330 |
| 2003/0129186 A1 | | 7/2003 | Beliveau et al. |
| 2005/0032848 A1 | | 2/2005 | Aquino et al. |
| 2005/0215561 A1 | | 9/2005 | Ghosh et al. |
| 2005/0288375 A1 | | 12/2005 | Hobden et al. |

FOREIGN PATENT DOCUMENTS

| | | |
|---|---|---|
| JP | 2004-520289 | 7/2004 |
| JP | 2007-529551 | 10/2007 |
| WO | 02/44142 | 6/2002 |
| WO | 2005/092307 | 10/2005 |

OTHER PUBLICATIONS

Supplementary European Search Report for European Appln. No. 07762687 mailed Jul. 2, 2009.
Deane et al. "RAGE mediates amyloid-beta peptide transport across the blood-brain barrier and accumulation in brain" *Nature Medicine*, vol. 9, No. 7, pp. 907-913 (Jul. 2003).
Deane et al. "RAGE (yin) versus LRP (yang) balance regulates Alzheimer amyloid beta-peptide clearance through transport across the blood-brain barrier" *Stroke*, vol. 35, No. 11, suppl. 11, pp. 2628-2631 (Nov. 2004).
Deane et al. "Tertiary amides block RAGE-mediated Aβ transport into brain in a mouse model of AD" presented at 36th *Annual Meeting of the Society for Neuroscience*, abstract 412.3 (Oct. 2006).
Herting et al. "Milacemide and other drugs active at glutamate NMDA receptors as potential treatment for dementia" *Annals of the New York Academy of Science*, vol. 640, No. 237-240 (1991).
International Search Report for PCT/US2007/002220 dated Dec. 17, 2007.
Written Opinion for PCT/US2007/002220 dated Dec. 17, 2007.
English translation of Office Action for Japanese Application No. 2008-552,448, mailed Aug. 14, 2012 (four pages).

* cited by examiner

*Primary Examiner* — San-Ming Hui
*Assistant Examiner* — Kathrien Cruz
(74) *Attorney, Agent, or Firm* — Nixon & Vanderhye PC (57) ABSTRACT

Small molecules are used to inhibit specific receptor-ligand interaction between Alzheimer's amyloid-β peptide (Aβ) and Receptor for Advanced Gly-cation Endproducts (RAGE). Objectives include treating Alzheimer's disease and other pathologies involving cerebral amyloid angiopathy; improving blood flow to or within the brain; decreasing the level of Aβ in the brain; reducing neuropathology associated with Alzheimer's disease; reducing inflammation and/or oxidant stress in the brain; improving memory and/or learning; treating other conditions involving Aβ/RAGE interaction at the blood-brain barrier, RAGE-mediated transport of Aβ into the brain, or RAGE activation in brain vasculature and/or brain parenchyma (e.g., diabetic complications); or any combination thereof.

14 Claims, 8 Drawing Sheets

INHIBITING AMYLOID-BETA PEPTIDE/RAGE INTERACTION AT THE BLOOD-BRAIN BARRIER

CROSS-REFERENCE TO RELATED APPLICATIONS

This is a U.S. national-stage application of Int'l Appln. No. PCT/US2007/002220 under 35 U.S.C. 371, filed Jan. 26, 2007; which claims the benefit of provisional Appln. No. 60/762,117, filed Jan. 26, 2006. The entire contents of which are hereby incorporated by reference in this application.

FEDERALLY-SPONSORED RESEARCH OR DEVELOPMENT

This invention was made with federal support under NIH grant AG200415, which was awarded by the Department of Health and Human Services. The U.S. Government has certain rights in the invention.

BACKGROUND OF THE INVENTION

The invention relates to inhibiting specific receptor-ligand interaction between Alzheimer's amyloid-β peptide (Aβ) and the Receptor for Advanced Glycation Endproducts (RAGE).

A number of genetic, cellular, biochemical, and animal studies suggest accumulation of amyloid β-peptide (Aβ) in the brain is the key event in Alzheimer's disease (AD), while the rest of the disease process, including formation of neurofibrillar tangles results from an imbalance between Aβ production and Aβ clearance (Hardy & Selkoe, 2002; Tanzi et al., 2004; Zlokovic, 2005). Aβ is neurotoxic (Walsh et al., 2002; Kayed et al., 2003; Gong et al., 2003) and deposits as amyloid in brain parenchyma and brain vessels in patients with sporadic AD and familial forms of AD (FAD). The mechanisms responsible for Aβ production, i.e., the proteolytic enzymes β- and γ-secretases which cleave Aβ from its larger precursor protein (APP), have been characterized (Selkoe, 1998; Vassar et al., 1999) and their respective inhibitors developed. Increased Aβ production, however, can explain only a small number of early onset FAD cases bearing inherited mutations in the APP gene (i.e., Swedish mutation) or presenilins 1 or 2 genes, but does not contribute to late-onset AD or >98% of all AD cases (Selkoe, 2001; Holtzman & Zlokovic, 2006). According to a new emerging concept, reduced Aβ clearance and/or its increased influx and re-entry into the brain from circulation via transport across the blood-brain barrier (BBB) may be responsible for Aβ brain accumulations in sporadic AD (Tanzi et al., 2004, Zlokovic, 2005; Holtzman & Zlokovic, 2006).

Recent evidence indicates that Aβ within the intravascular space is linked to deposited Aβ in the brain suggesting that transport of Aβ from blood to brain and from brain to blood across the blood-brain barrier (BBB) regulates brain Aβ (Shibata et al., 2000; De Mattos et al., 2002a; De Mattos et al., 2002b; Bading et al., 2002; Mackic et al., 2002; Carro et al., 2002; Deane et al., 2003; Deane et al., 2004; Tanzi et al., 2004; Zlokovic, 2005; Holtzman & Zlokovic, 2006). Numerous studies in animal models (reviewed by Deane et al., 2004; Holtzman & Zlokovic, 2006) and some studies in AD patients demonstrating increased levels of Aβ on plasma lipoproteins and proteins (Matsubara et al., 1999; Kuo et al., 1999), have suggested that re-entry of circulating Aβ into the brain via transport across the BBB is an important source of brain Aβ. High plasma levels of Aβ40/42 have been determined in mouse models of Aβ under basal conditions, e.g., APPsw$^{+/-}$ mice (Kawarabayashi et al., 2001) or after treatment with Aβ peripheral binding agents, e.g., anti-Aβ antibodies (De Mattos et al., 2002a), sRAGE (Deane et al., 2003), which confirms the link between intravascular and brain Aβ.

RAGE is a multiligand receptor in the immunoglobulin superfamily which binds a broad repertoire of ligands including Aβ (Stern et al., 2002). In mature animals there is relatively little expression of RAGE in most tissues, whereas deposition of ligands triggers RAGE expression. When Aβ accumulates in AD or in animal models of AD, RAGE expression increases particularly in cerebral microvessels, a site of the BBB in vivo (Yan et al., 1996; Deane et al., 2003; LaRue et al., 2004; Donahue et al., 2004). RAGE binds soluble Aβ in the nano-molar range, and mediates pathophysiologic cellular responses consequent to ligation by Aβ (Yan et al., 1996; Mackic et al., 1998; Yan et al., 2000). These include transport of pathophysiologically relevant concentrations of plasma Aβ across the BBB, neurovascular stress, and reduction in the cerebral blood flow (CBF) (Deane et al., 2003; LaRue et al., 2004). Deletion of the RAGE gene protects the CNS pool of Aβ from influences of its peripheral pool by eliminating re-entry of circulating Aβ into the brain, whereas systemic treatment with soluble RAGE (sRAGE) sequesters circulating Aβ and reduces brain accumulation and deposition of Aβ in a mouse model of AD (Deane et al., 2003). Thus, compounds which block Aβ/RAGE interaction at the BBB may also block re-entry of Aβ to the brain, reduce Aβ-related pathology, and improve CBF dysregulation and cognitive decline, which should have important beneficial therapeutic effects in AD.

Compounds to inhibit Aβ/RAGE interaction, compositions containing one or more of those compounds, and methods of treatment are taught herein to be applicable to Alzheimer's disease and other conditions involving Aβ-RAGE interaction at the blood-brain barrier, RAGE-mediated transport of Aβ into the brain, and/or RAGE activation RAGE activation in brain vasculature or brain parenchyma. Other advantages of the invention are discussed below or would be apparent to a person skilled in the art from that discussion.

SUMMARY OF THE INVENTION

The invention is used to inhibit specific receptor-ligand interaction between Aβ and RAGE. This may be used to manufacture a medicament (e.g., therapeutic and/or prophylactic composition) to treat Alzheimer's disease or other conditions involving Aβ-RAGE interaction at the blood-brain barrier, RAGE-mediated transport of Aβ into the brain, and/or RAGE activation RAGE activation in brain vasculature or brain parenchyma. The amount or concentration Aβ in the brain is decreased, neuropathology associated with Alzheimer's disease is reduced, cerebral blood flow is increased, memory and/or learning is improved, or any combination thereof. In particular, compounds such as tertiary amides $R_1(CO)NR_2R_3$ and compositions containing one or more compounds are considered embodiments of the invention. $R_1$ may be an electron-deficient aryl moiety (e.g., aryl moiety substituted with one or more electron withdrawing groups, such as mono- or di-halide and mono- or di-nitro). $R_2$ may be a hydrophobic hydrocarbon moiety (e.g., straight or branched aliphatic, alicyclic such as cyclohexyl, straight or branched acyclic or cyclic olefin, straight or branched acyclic or cyclic acetylene, aryl-containing, and/or amine-containing C4-C18 hydrocarbon moiety which is optionally substituted). $R_3$ may be an electron-rich aryl moiety (e.g., furanyl, pyrrolyl, benzyl, phenyl, alkylphenyl, alkoxy-phenyl, naphthyl, benzofuryl, indyl, or quinolyl moiety which is optionally substituted)

with or without a C1-C4 alkyl (e.g., straight or branched) or heteroaromatic linker. For example, one or more compounds may be manufactured as a medicament or in a pharmaceutical composition.

Further aspects of the invention will be apparent to a person skilled in the art from the following detailed description and claims, and generalizations thereto.

BRIEF DESCRIPTION OF THE DRAWINGS

FIG. 2 shows that the FPS1, FPS2, and FPS3 compounds block Aβ40/RAGE interaction. (A) $^{125}$I-Aβ40 specific binding on RAGE-transfected CHO cells (square) or mock-transfected CHO cells (triangle) at 4° C. Compounds FPS1, FPS2, and FPS3 are high-affinity competitive inhibitors of Aβ-RAGE binding on RAGE-transfected CHO cells as indicated by the low nM values of their inhibitory constants (Ki) (B) and the respective Ki/Kd ratios (C) (Kd is the binding constant of Aβ to RAGE from FIG. 2A). Thiobarbituric acid reactive substance (TBARS) generation (D) and NF-κB activation (E) at 1 μM Aβ40 were inhibited in the presence of FPS2 at 50 nM or 500 nM. (F) FPS2 blocked Aβ40/soluble RAGE interaction in a cell-free system in vitro, as determined by ELISA. The statistical significance of differences is shown in FIGS. 2B-2D and 2F. Data are means±s.e.m., n=3 per group.

FIG. 9 shows the chemical structures of N1A2B1 (N-benzyl-4-chloro-N-cyclohexyl-benzamide); N1A2B2 (N-benzyl-2,4-dichloro-N-cyclohexyl-benzamide); N2A1B1 (4-chloro-N-(3-methyl-butyl)-N-phenethyl-benzamide); N2A2B2 (N-benzyl-2,4-dichloro-N-(3-methyl-butyl)-benzamide); N2A2B3 (N-benzyl-N-(3-methyl-butyl)-3,5-dinitro-benzamide); N2A2B4 (N-benzyl-N-(3-methyl-butyl)-3-nitro-benzamide); N2A2B5 (N-benzyl-4-chloro-N-(3-methyl-butyl)-3-nitro-benzamide); N3A2B2 (N-benzyl-2,4-dichloro-N-(1-ethyl-propyl)-benzamide); N3A2B3 (N-benzyl-N-(1-ethyl-propyl)-3,5-dinitro-benzamide); N3A2B5 (N-benzyl-4-chloro-N-(1-ethyl-propyl)-3-nitro-benzamide); N4A2B2 (N-benzyl-2,4-dichloro-N-(3-phenyl-propyl)-benzamide); and N4A2B5 (N-benzyl-4-chloro-3-nitro-N-(3-phenyl-propyl)-benzamide). The mass for each compound is shown next to the structure.

DESCRIPTION OF SPECIFIC EMBODIMENTS OF THE INVENTION

RAGE is a multiligand receptor in the immunoglobulin superfamily which binds a broad repertoire of ligands including neurotoxic Aβ. RAGE biology is largely dictated by the expression or accumulation of its ligands. In mature animals there is relatively little expression of RAGE in most tissues, whereas deposition of ligand triggers receptor expression. When pathogenic Aβ accumulates in Alzheimer's disease (AD) and/or in transgenic mouse models of AD, RAGE expression increases in the brain, particularly in cerebral microvessels, a site of the blood-brain barrier (BBB) in vivo, as we and others have reported. We showed that overexpression of RAGE at the BBB increases influx of circulating Aβ into the brain, which is associated with expression of proinflammatory cytokines, neurovascular stress, and reduction in the cerebral blood flow (CBF). Deletion of the RAGE gene suppresses Aβ influx (i.e., transport) across the BBB into the brain, reduces neurovascular stress, and improves CBF dysregulation. Systemic treatment with soluble RAGE (sRAGE) sequesters circulating Aβ prevents its transport and re-entry into the brain and reduces its brain accumulation and deposition in the mouse model of AD. Thus, we hypothesized that a compound which blocks Aβ/RAGE interaction at the BBB will inhibit re-entry and should have beneficial therapeutic effects in Alzheimer's disease.

Figure 1:
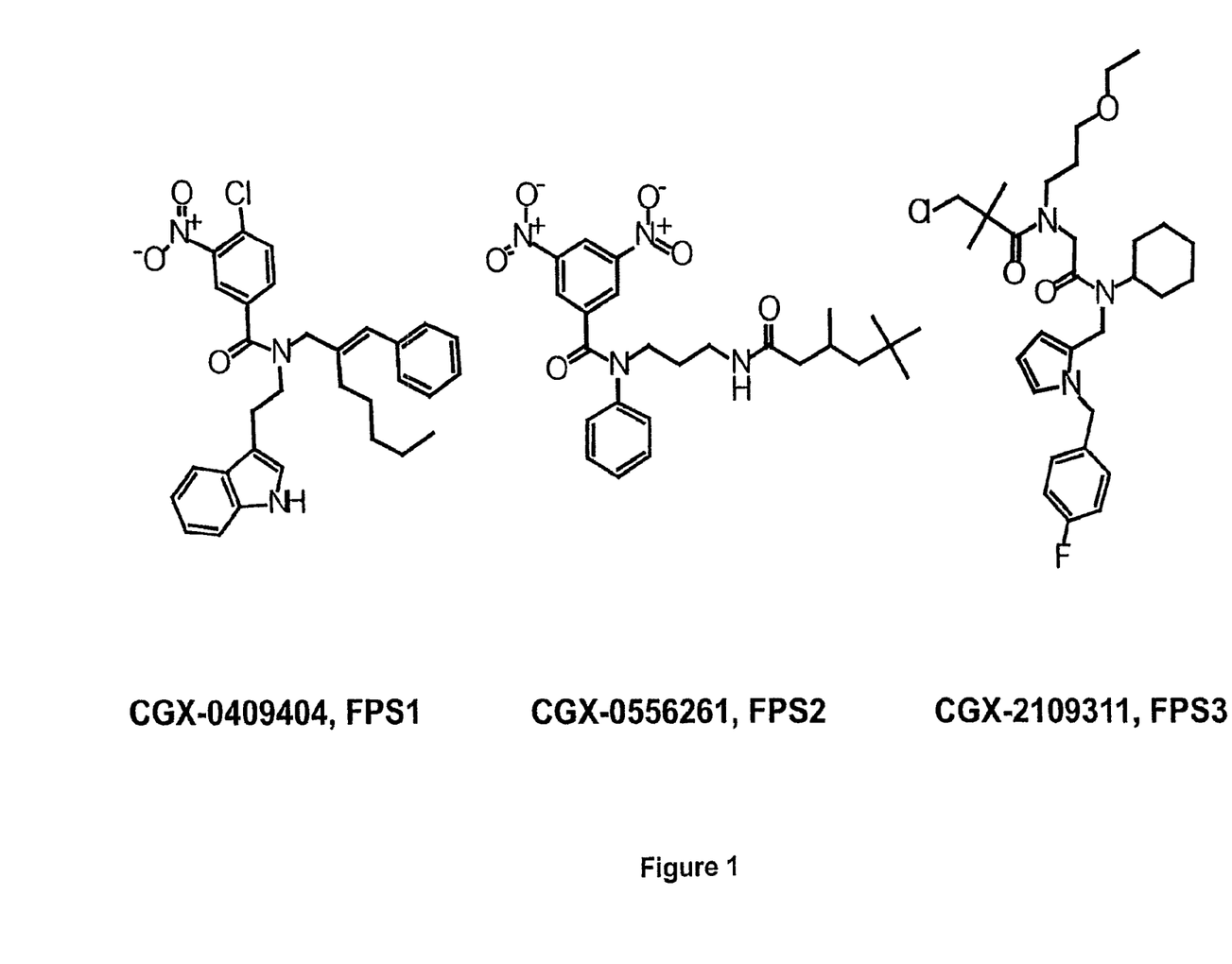
FIG. 1 shows the chemical structures of FPS1 (3-chloro-N-[2-[cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl)-propanamide); FPS2 (3,5-dinitro-N-phenyl-N-[3-[(3,5,5-trimethyl-1-oxohexyl)amino]propyl]-(9Cl)-benzamide); and FPS3 (4-chloro-N-[2-(1H-indo-3-yl)-ethyl]-3-nitro-N-(2-pentyl-3-phenyl-allyl)-benzamide).

By a primary screen on RAGE-transfected Chinese hamster ovary (CHO) cells, three high-affinity inhibitors of Aβ/RAGE interaction were identified out of seven hits from a diverse library of 5000 small organic compounds. These three compounds (FPS1, FPS2, and FPS3) share several structural characteristics (FIG. 1). All three are tertiary amides substituted with a large, hydrophobic hydrocarbon moiety and a monosubstituted aromatic moiety. Linkage to the monosubstituted aromatic is either direct (FPS2) or via an alkyl (FPS1) or heteroaromatic (FPS3) spacer. Two of the compounds also feature a highly electron-poor substituted benzene ring (3-nitro, 4-chloro for FPS1; 3,5-dinitro for FPS2).

Figure 2:
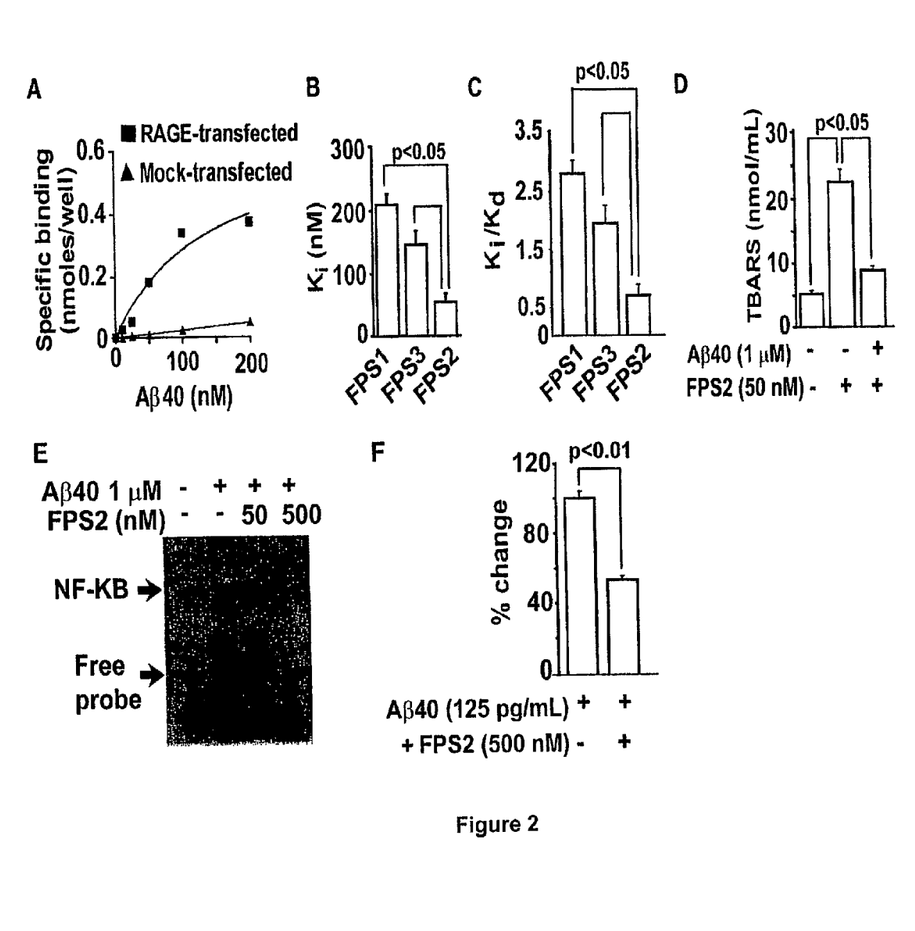

FIG. 2A shows saturable binding of $^{125}$I-Aβ40 to RAGE in RAGE-transfected CHO cells at 4° C.; the Kd (binding constant) was 75±8 nM as we reported (Mackic et al., 1998). There was no binding on mock-transfected cells. All inhibit Aβ-RAGE binding competitively with the Ki (inhibitory constant) in descending order of affinity FPS2>FPS3>FPS1 (FIG. 2B) close to the Kd (binding constant) of Aβ40 binding to RAGE in RAGE-transfected CHO cells. Their respective Ki/Kd ratios were 0.45, 1.6, and 2.6, respectively, (FIG. 2C) where Ki is the compound's inhibitory constant and Kd is the Aβ-RAGE binding constant. We focused on FPS2 as the highest affinity blocker. In RAGE-transfected CHO cells, FPS2 inhibits Aβ/RAGE-induced oxidant stress (FIG. 2D) and translocation of nuclear factor kappa B (NF-κB) (FIG. 2E). It also inhibits Aβ/RAGE interaction in a cell-free system in vitro (FIG. 2F).

Figure 3:
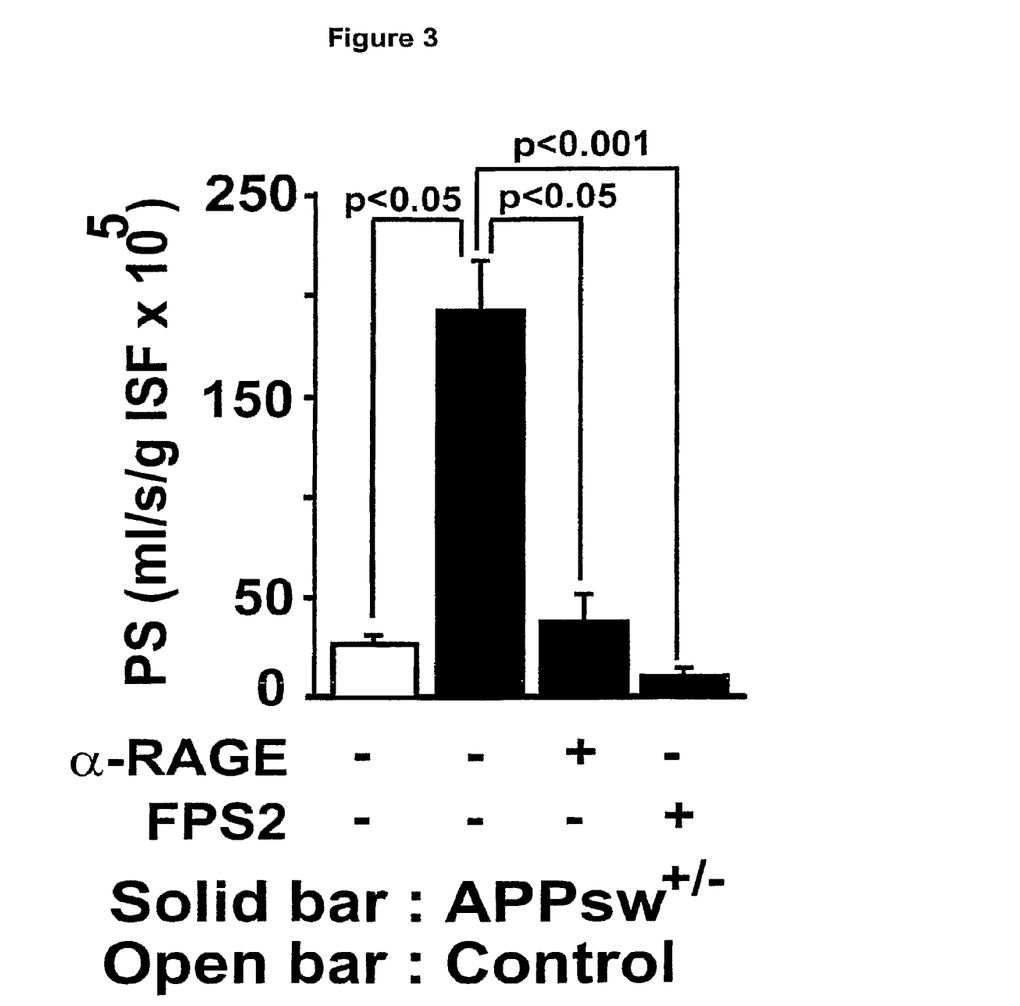
FIG. 3 shows transport of $^{125}$I-Aβ40 at 1.5 nM (corresponding to the plasma concentration in APPsw$^{+/-}$ mice) across the BBB in vivo in 5-6 month old APPsw$^{+/-}$ mice (closed bars) and age-matched controls (open bar) determined with the arterial brain perfusion technique in the absence or presence of RAGE-specific IgG (α-RAGE, 20 μg/ml) or FPS2 (4.8 μg/ml). The statistical significance of differences is shown. Data are means±s.e.m., n=3-4 per group.

An arterial vascular brain perfusion technique (LaRue et al., 2004) was used to determine whether FPS2 blocks RAGE-mediated transport of circulating $^{125}$I-labeled Aβ40 across the BBB in 4-6 month old APPsw$^{+/-}$ mice. We and others have reported that expression of RAGE in brain microvessels in these mice is increased by about 5-fold compared to the littermate controls (Deane et al., 2003; Donahue et al., 2004). FIG. 3 shows that RAGE-specific IgG at high concentration of 20 μg/ml of plasma arterial inflow inhibits by >80% Aβ transport across the BBB, whereas FPS2 at 4.8 μg/ml abolishes Aβ transport across the BBB resulting in 100% inhibition (FIG. 3). This data suggests that FPS2, and possibly its related compounds, have potential to block re-entry and influx of circulating Aβ across the BBB in vivo, which in an animal model of AD should reduce Aβ brain accumulation and amyloid pathology and improve CBF dysregulation and behavior.

Compounds of the invention may be used as a medicament or to formulate a composition with one or more of the utilities disclosed herein. A "pharmaceutical" composition further contains a physiologically-acceptable vehicle and is produced under aseptic conditions. The composition may further comprise components useful for delivering the compound to its site of action. Choice and addition of such vehicles and carriers to the composition are within the level of skill in the art. Compounds or compositions may be administered in vitro to cells in culture, in vivo to cells in the body, or ex vivo to cells outside of the subject that may later be returned to the body of the same subject or another. The subject is a human in need of treatment (e.g., a patient affected by Alzheimer's disease and its progression, or at risk for its development) or an animal model for Alzheimer's disease and its pathogenesis.

The pharmaceutical composition may be administered as a formulation adapted for delivery to systemic circulation, blood-brain barrier, brain vasculature, or brain parenchyma. Alternatively, the composition may be administered to culture medium. In addition to the active compound, such compositions may contain physiologically-acceptable vehicles, carriers, and other ingredients known to facilitate administration and/or enhance uptake (e.g., saline, dimethyl sulfoxide, lipid, polymer, affinity-based cell specific-targeting systems). The composition may be incorporated in a gel, sponge, or other permeable matrix (e.g., formed as pellets or a disk) and placed in proximity to the endothelium for sustained, local release. It may be administered in a single dose or in multiple doses which are administered at different times.

The pharmaceutical composition may be administered by any known route. By way of example, the composition may be administered by a mucosal, pulmonary, topical, or other localized or systemic route (e.g., enteral and parenteral). The term "parenteral" includes subcutaneous, intra-arterial, intradermal, intramuscular, intrathecal, intravenous, and other injection or infusion techniques, without limitation. In particular, an effective amount of one or more compounds is present where Aβ and RAGE interact.

Suitable choices in amounts and timing of doses, formulation, and routes of administration can be made with the goals of achieving a favorable response in the subject with Alzheimer disease or at risk thereof (i.e., efficacy), and avoiding undue toxicity or other harm thereto (i.e., safety). Therefore, "effective" refers to such choices that involve routine manipulation of conditions to achieve a desired effect.

A bolus administered over a short time once a day is a convenient dosing schedule. Alternatively, the effective daily dose may be divided into multiple doses for purposes of administration, for example, two to twelve doses per day. Dosage levels of active ingredients in a pharmaceutical composition can also be varied so as to achieve a transient or sustained concentration of the compound in a subject, especially in and around vascular endothelium of the brain or systemic circulation, and to result in the desired therapeutic or prophylactic response. But it is also within the skill of the art to start doses at levels lower than required to achieve the desired therapeutic or prophylactic effect and to gradually increase the dosage until that effect is achieved.

The amount of compound administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration; and the like. For systemic administration, passage of the compound or its metabolite through the blood-brain barrier should not be critical. It should be understood that the specific dose level to be achieved for any particular subject may depend on a variety of factors, including age, gender, health, medical history, weight, combination with one or more other drugs, and severity of disease.

The term "treatment" of Alzheimer disease refers to, inter alia, reducing or alleviating one or more symptoms in a subject, preventing one or more symptoms from worsening or progressing, promoting recovery or improving prognosis, and/or preventing disease in a subject who is free therefrom as well as slowing or reducing progression of existing disease. For a given subject, improvement in a symptom, its worsening, regression, or progression may be determined by objective or subjective measure. Efficacy of treatment may be measured as an improvement in morbidity or mortality. Preventative methods (e.g., preventing development of disease or the incidence of relapse) are also considered treatment.

The amount which is administered to a subject is preferably an amount that does not induce toxic effects which outweigh the advantages which result from its administration. Further objectives are to reduce in number, diminish in severity, and/or otherwise relieve suffering from the symptoms of the disease as compared to recognized standards of care.

Production of compounds according to present regulations will be regulated for good laboratory practices (GLP) and good manufacturing practices (GMP) by governmental agencies (e.g., U.S. Food and Drug Administration and European Medicines Agency). This requires accurate and complete record-keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

RAGE at the BBB is the major influx receptor for Aβ mediating its transport, retention and accumulation in the brain, cytokine response, and suppression of the CBF (Deane et al., 2003; LaRue et al., 2004). Our studies here indicate that RAGE at the BBB is a major therapeutic target for inhibiting the pathogenic consequences of Aβ-vascular interactions, including development of cerebral amyloidosis. These data strongly support our proposal that treatment of APPsw$^{+/-}$ mice with FPS2 or the related compounds FPS3 and FPS1 will (1) prevent development of β-amyloidosis, (2) improve dysregulated CBF, and (3) improve behavior. The inhibitory effect of FPS2 on RAGE-mediated transport of Aβ across the BBB in vivo in APPsw$^{+/-}$ mice was characterized. The therapeutic effects of FPS2 on Aβ pathology, CBF dysregulation, and behavior in APPsw$^{+/-}$ mice was also evaluated. Other compounds of the invention may be similarly characterized for their beneficial effect(s) on Alzheimer's disease.

According to the amyloid hypothesis, Aβ accumulation in the brain is a chief event contributing to pathogenesis AD (Hardy & Selkoe, 2002). Recent evidence indicates that Aβ within the intravascular space is linked to Aβ deposited in the brain. This suggests that transport of Aβ between the blood-to-brain and brain-to-blood paths across the BBB regulates the level of Aβ in the brain (Deane et al., 2003; Deane et al., 2004; Tanzi et al., 2004; Zlokovic, 2005, Holtzman & Zlokovic, 2006).

At the BBB, RAGE mediates transport of Aβ into the CNS which is associated with neurovascular stress, accumulation of Aβ in the brain, and development of Aβ-related pathology (Deane et al., 2003; LaRue et al., 2004; Donahue et al., 2004). Increased expression of RAGE in cerebral microvessels at the BBB in AD and in animal models of AD may result in increased transport of plasma Aβ into the brain, reduction in CBF, and expression of proinflammatory cytokines. Deletion of the RAGE gene eliminates influx of circulating Aβ into the brain as well as Aβ-induced changes in CBF and inflammation. A soluble form of RAGE (sRAGE) prevents accumulation of Aβ in the brain in a mouse model of AD. We hypothesize here that compounds which inhibit RAGE/Aβ interaction at the BBB will act as Aβ-lowering agents by preventing Aβ effects on transport, neuroinflammation, hypoperfusion, and accumulation in the brain.

The therapeutic effect of compounds of the invention can be determined in an animal model of AD. APPsw$^{+/-}$ mice can be treated with one or more compounds as described for sRAGE (see Deane et al., 2003). Mice can be sacrificed to determine Aβ load, Aβ40 and Aβ42 levels, and soluble/insoluble fractions. The results confirmed our hypothesis that the compounds reduce Aβ accumulation and amyloid load substantially. APPsw$^{+/-}$ mice have reduced CBF responses to whisker stimulation (Iadecola et al., 1999) and reduced resting CBF (Deane et al., 2003), whereas blocking Aβ/RAGE interaction increases CBF in AD mice (Deane et al., 2003). The CBF responses to whisker stimulation can be measured in APPsw$^{+/-}$ mice to determine the effects of treatment on brain activation-induced increases in CBF. A battery of behavioral tests can be performed: Barnes maze for spatial learning and memory (Bach et al., 1995); force-plate actometer for general activity, spatial patterning, locomotion, ataxia, tremor, and seizure (Zarcone, 2001); and operant chamber for attention and spatial alternation in learning and memory (Markowski et al., 2000).

Although toxicity of the compounds has not be observed in assays (i.e., TUNEL, Hoechst staining, LDH release, negative WST-8), it is possible that one or all compounds are toxic in vivo. To determine if compounds are toxic in vivo, blood counts, hemoglobin level, electrolytes, glucose, blood pressure, heart rate, respiration, blood gasses, and pH will be determined. Kidney function (urea, creatinine), liver enzymes, general activity, spatial patterning, locomotion, ataxia, tremor, attention, and spatial alternation in learning and memory may also be tested. It is possible that compounds are not specific inhibitors of Aβ-RAGE binding. To address this issue, in vitro analysis may be performed using a cell-free system with immobilized LRP, apolipoproteins E and J, α2-macroglobulin, and other possible receptors and binding proteins for Aβ to confirm the specificity of the compounds to prevent or disrupt Aβ-RAGE binding.

Figure 4:
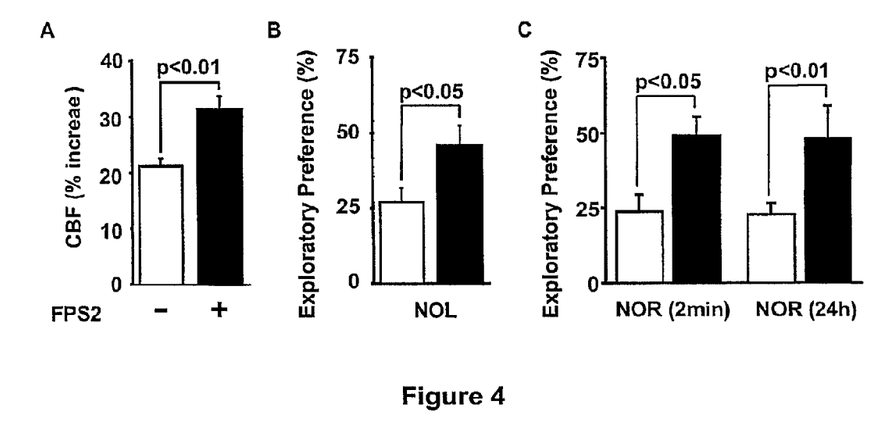
FIG. 4 shows that FPS2 treatment improves functional outcome in APPsw$^{+/-}$ mice. (A) Percent increase in cerebral blood flow (CBF) in response to brain activation in mice treated with vehicle (open bar) or FPS2 (closed bar). (B-C) novel object location (B) and novel object recognition (C) expressed as percent exploratory preference in APPsw$^{+/-}$ mice treated with vehicle (open bar) or FPS2 (closed bar). FPS2 (1 mg/kg per day) was intraperitoneally administered for two months beginning at the age of 8 months old mice. Values are means±s.e.m, n=5-6 per group.
Figure 5:
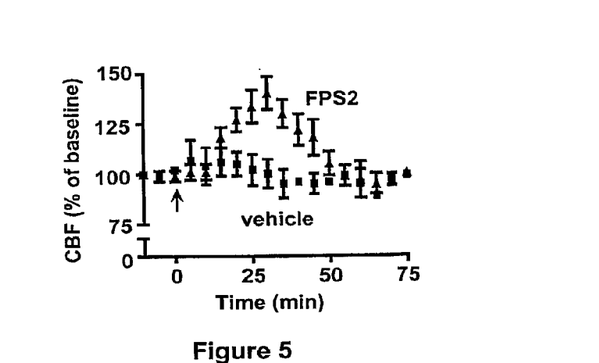
FIG. 5 shows that resting cerebral blood flow changes in APPsw$^{+/-}$ mice after FPS2 administration. Cerebral blood flow changes expressed as a percentage of baseline recorded over a 90 min period in mice administered FPS2 (filled triangle) or vehicle (filled square). FPS2 (1 mg/kg) was administered intravenously (arrow) as a bolus in 7-9 months old mice. Values are means±s.e.m, n=3 per group.

APPsw$^{+/-}$ mice were treated with FPS2 (1 mg/kg) or with vehicle daily by intraperitoneal injection for two months starting at 8 months old. At the end of the treatment period functional changes in cerebral blood flow (CBF) to brain activation, and memory tests were determined. Brain and plasma Aβ levels were also determined in FPS2 and vehicle treated mice. Compared to vehicle chronic treatment with FPS2 increased CBF during brain activation by about 50%, and significantly increased memory determined by novel object location and novel object recognition (FIG. 4). To establish whether FPS2 changes resting CBF, acute studies were also conducted. In these studies, an intravenous bolus injection of FPS2 (1 mg/kg) in APPsw$^{+/-}$ (7-9 months old) transiently increased resting CBF by about 35% and peaked after 25-30 min (FIG. 5).

Figure 6:
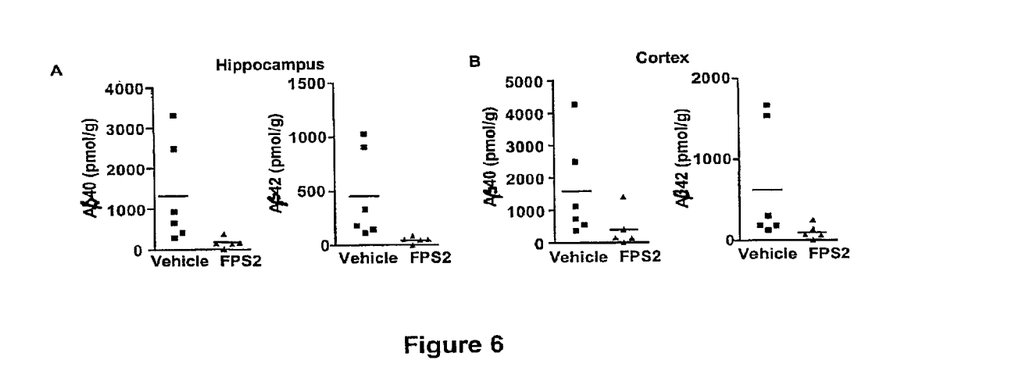
FIG. 6 shows that FPS2 clears Aβ from brains in APPsw$^{+/-}$ mice. A-B, Aβ40 and Aβ42 levels in hippocampus (A) cortex (B) of APPsw$^{+/-}$ mice treated with vehicle (filled square) or FPS2 (filled triangle). FPS2 (1 mg/kg per day) was administered intraperitoneally to mice for two months beginning at the age of 8 months. Values are means±s.e.m, n=5-6 per group.
Figure 7:
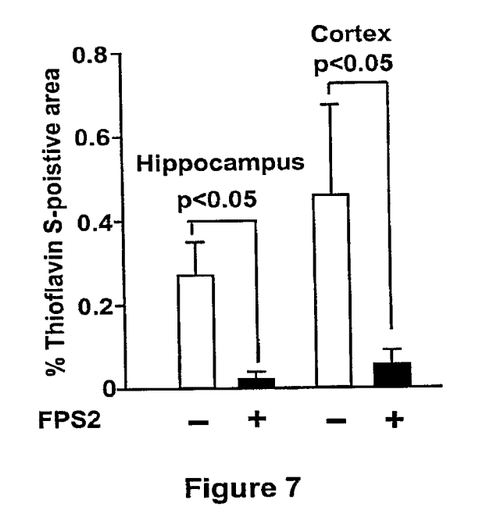
FIG. 7 shows that FPS2 reduces amyloid load clears in brains of APPsw$^{+/-}$ mice. Amyloid load hippocampus and cortex of APPsw$^{+/-}$ mice treated with vehicle (open bars) or FPS2 (closed bars). FPS2 (1 mg/kg per day), was administered intraperitoneally to mice for two months beginning at the age of 8 months. Values are means±s.e.m, n=5-6 per group.

In the chronic-treated mice, Aβ40 and Aβ42 levels in the hippocampus were reduced by about 85% and 90%, respectively, in the FPS2-treated mice compared to vehicle (FIG. 6A). Similarly, Aβ40 and Aβ42 levels in the cortex were reduced by about 70% and 80%, respectively (FIG. 6B). Thioflavin-S positive areas (amyloid load) in the hippocampus and cortex were significantly reduced by about 85% in the FPS2 treated mice compared to vehicle (FIG. 7).

Figure 8:
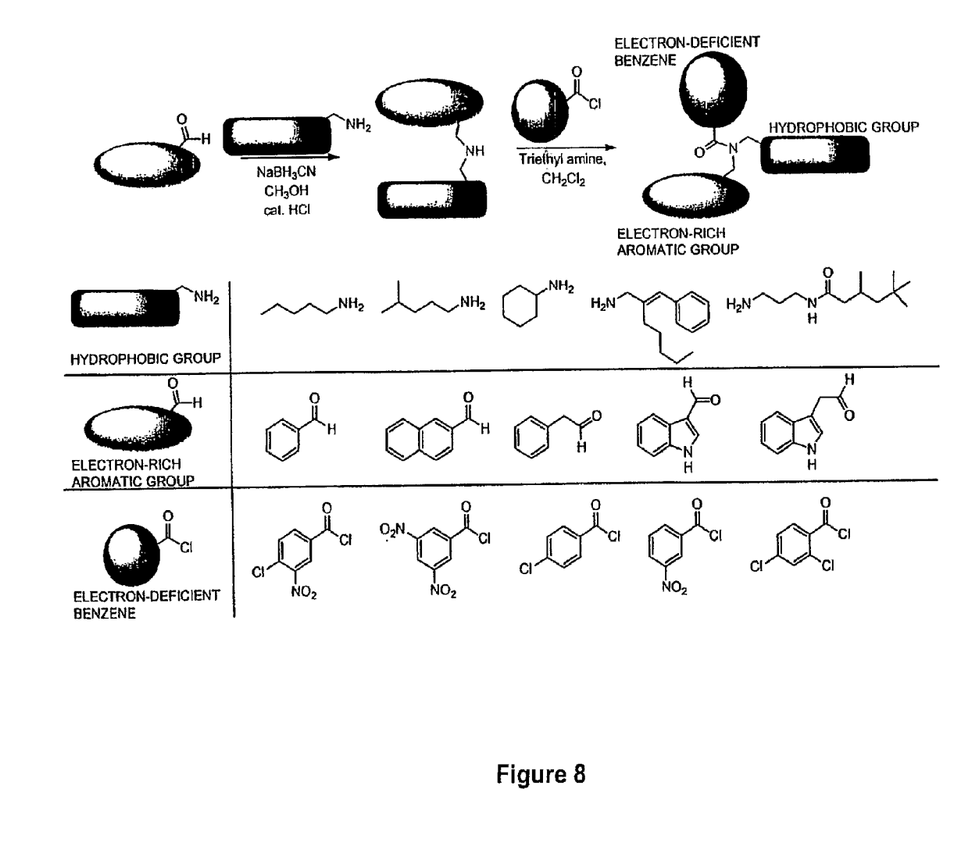
FIG. 8 illustrates construction of a combinatorial library designed to test structure-activity relationships based on FPS1, FPS2, and FPS3.

It is possible that the initial three compounds are not effective enough in inhibiting Aβ/RAGE interaction and that other compounds in the family will be more effective. Therefore, building on the structural commonalities of FPS1 and FPS2, a structure-activity study was carried out by synthesizing and analyzing a library of 125 structurally-related compounds. FIG. 8 illustrates construction of a combinatorial library designed to test structure-activity relationships based on FPS1, FPS2, and FPS3. For example, the tertiary amides $R_1(CO)NR_2R_3$ may be a product of $R_1$ (e.g., 2-fluorobenzene, 4-fluorobenzene, 2,4-difluorobenzene, 3-chloro-4-fluorobenzene, 4-chloro-3-fluorobenzene, 3,5-difluorobenzene); $R_2$ (e.g., ethyl, propyl, butyl, dimethyl-propane, hexyl, heptyl, octyl); $R_3$ (o-methoxy benzene, p-methoxy benzene, 2,4-dimethoxybenzene, 3,4-dimethoxybenzene, 3,4,5-trimethoxybenzene, 4-trifluoromethylbenzene); or any combination thereof. These studies should result in discovery of new Aβ lowering agent(s) which can inhibit RAGE-Aβ interaction at the BBB and its pathophysiological consequences including net blood-to-brain transport of Aβ, neuroinflammation, and accumulation of Aβ in the brain.

Figure 9:
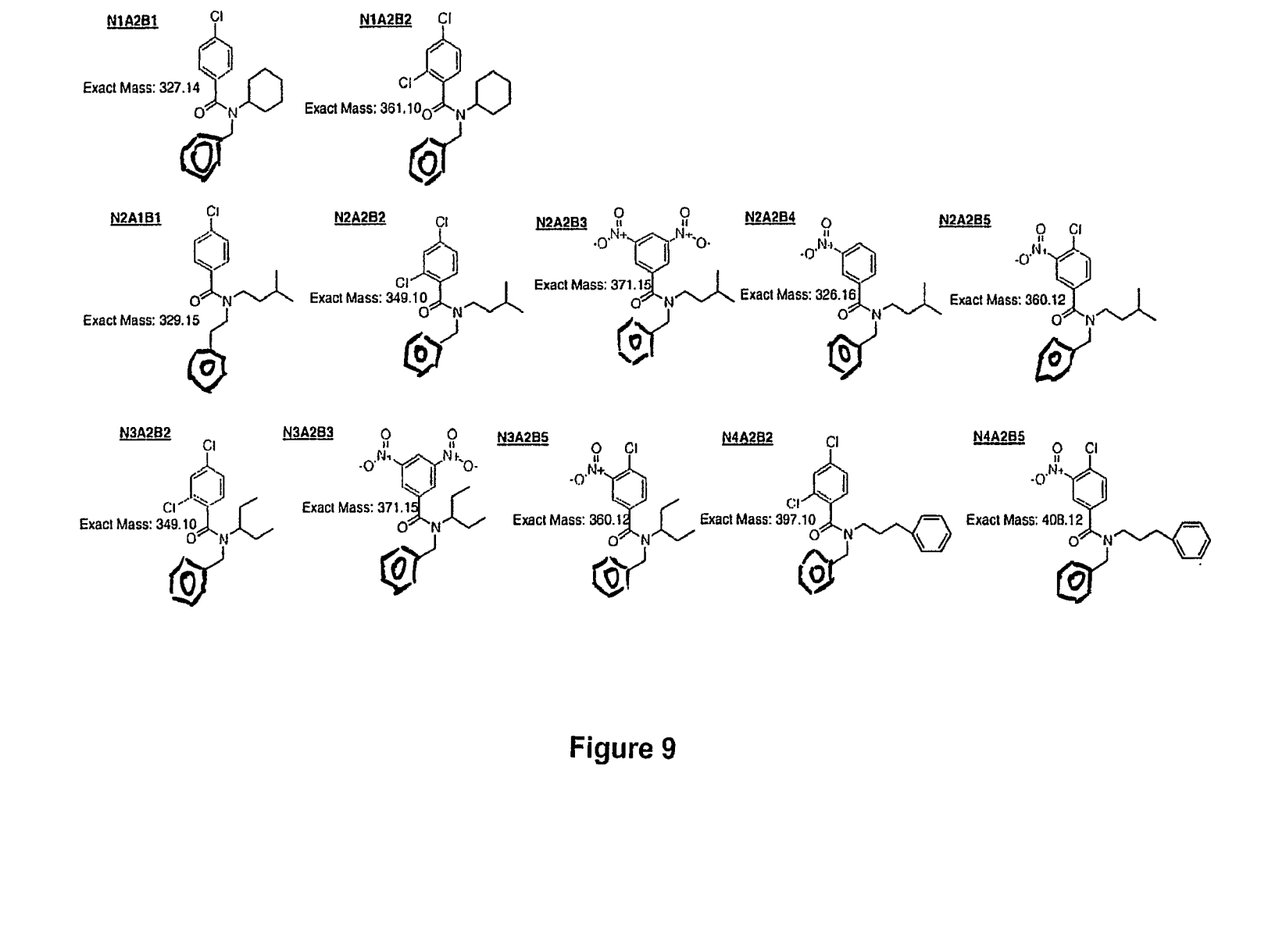

Compounds were synthesized in parallel using semiautomated chemical reactions. Five commercially-available aromatic aldehydes were condensed in reductive amination reactions with five hydrophobic amines to form 25 secondary amines. Parallel acylation of these 25 secondary amines with five aromatic acyl chlorides provided the final 125-compound library of tertiary amides. The identity of compounds was verified by mass spectrometry (FIG. 9). Purity was assessed by reverse-phase gradient HPLC. Library members isolated with purity <95% were subjected to preparative HPLC purification prior to assay.

Animals. APPsw$^{+/-}$ (Tg2576) mice were from Taconic Farms (Germantown, N.Y.). Mice were housed under standard conditions (12 hour light/dark cycle starting at 07:00 AM; 21±2° C.; 55±10% humidity) in solid-bottom cages on woodchip bedding. Mice were anesthetized by intraperitoneal injection with urethane (750 mg/kg) and α-chloralose (50 mg/kg). All procedures on mice were performed according to the NIH guidelines, which were approved by the University of Rochester's Committee on Animal Resources.

FPS2 chronic treatment of APPsw$^{+/-}$ mice. APPsw$^{+/-}$ mice (n=5-6 per group) were treated intraperitoneally with FPS2 (1 mg/kg per day) or saline for two months beginning at the age of 8 months. After two months of treatment, (i) the cerebral blood flow response to brain activation (whisker stimulation) was measured and (ii) behavioral tests including operant learning, novel object location (NOL), and novel object recognition (NOR) were performed. After these functional tests, the mice were sacrificed and their brains analyzed for Aβ40, Aβ42, and amyloid levels.

CBF response to brain activation. The CBF response to vibrissal stimulation in anesthetized APPsw$^{+/-}$ mice was measured by using laser-doppler flowmetry (Transonic Systems, BLF 21 D). The tip of the laser-doppler probe was stereotaxically placed 0.5 mm above the dura of the cranial window. The right vibrissae were cut to about 5 mm and stimulated by gentle stroking at 3-4 Hz, for 1 min with a cotton-tip applicator. Rectal temperature was maintained at 37° C. using a heated blanket (Homeothermic Blanket, Harvard Apparatus). The percentage increase in CBF due to vibrissal stimulation was obtained from the baseline CBF and averaged for the three trials.

Memory testing. The memory tests consisted of three phases: habituation, sample, and choice trials. Mice were first habituated to the empty test box. A sample trial (object exposure) consisted of placing a mouse into the test box which contained five different objects. The mouse was removed from the test box and after a delay (retention period) the mouse was placed back into the test box for a choice trial. A choice trial could consist of switching the location of two of the objects (Novel-Object Location (NOL) trial) or substituted one object with a new object (Novel-Object Recognition (NOR) trial). The time exploring the novel and familiar objects was scored by hand to provide discrimination.

Human Aβ40 and Aβ42. APPsw$^{+/-}$ mice were transcardially perfused with ice-cold heparinized saline and the brains removed. Hippocampus and cortex were homogenized in ice-cold guanidine buffer (5 M guanidine hydrochloride/ 50 mM TrisCl, pH 8.0) and used for human Aβ40 and Aβ42 determination. Briefly, brain (hippocampus and cortex) and plasma human Aβ40 and Aβ42 levels were determined using human specific ELISA kits KHB3481 and KHB3441, respectively, according to the manufacturer's instructions (Invitrogen, Carlsbad, Calif.). For human Aβ40 and Aβ42 ELISA assays, a monoclonal antibody specific against the NH$_2$-terminus of human Aβ was used as capturing antibody and a rabbit antibody specific for the COOH-terminus of either Aβ40 or Aβ42 was used as detecting antibody.

Amyloid load. Acetone-fixed cryostat brain slices (10 μm) were incubated with PBS containing 1% thioflavin S (Sigma Aldrich) and subsequently washed with 80% ethanol, 90% ethanol, and ddH$_2$O. The thioflavin S-positive amyloid load was determined using the IMAGE-PRO®-Plus software (Media Cybernetics).

FPS2 acute treatment of APPsw$^{+/-}$ mice. Resting CBF over the sensory-motor cortex was determined using laser-doppler flowmetry (Transonic Systems, BLF 21 D). The tip of the laser-doppler probe was stereotaxically placed 0.5 mm above the dura of the cranial window. 15 min after steady-state conditions was obtained FPS2 (1 mg/kg) or vehicle was administered intravenously (via the femoral vein) and CBF recorded for an additional 75 min. Rectal temperature was maintained at 37° C. using a heated blanket (Homeothermic Blanket, Harvard Apparatus). The percentage change in CBF from baseline was obtained. Values were expressed as mean±s.e.m. (n=3).

References

Bach at al. (1995) Cell 81:905-915
Bading et al. (2002) J. Drug Targeting 10:359-368
Begley & Brightman (2003) Prog. Drug Res. 61:39-78
Carro at al. (2002) Nature Med. 8:1390-1397
Deane et al. (2003) Nature Med. 9:907-913
Deane et al. (2004) Neuron 43:333-344
DeMattos et al. (2002a) Science 295:2264-2267
DeMattes at al. (2002b) J. Neurochem. 81:229-236
Donahue et al. (2004) in *The 9$^{th}$ In'l Conf. Alzheimer's Disease and Related Disorders*, Philadelphia
Gong et al. (2003) Proc. Natl. Acad. Sci. USA 100:10417-10422
Hardy & Selkoe (2002) Science 297:353-356
Holtzman & Zlokovic (2006) in *Alzheimer's Disease: Advances in Genetics, Molecular and Cellular Biology* (Sisodia & Tanzi, eds.) Springer
Iadecola et al. (1999) Nat. Neurosci. 2:157-161
Kawarabayashi et al. (2001) J. Neurosci. 21:372-381
Kayed et al. (2003) Science 300:486-489
Kuo et al. (1999) Biochem. Biophys. Res. Comm. 257:787-791
LaRue et al. (2004) J. Neurosci. Methods 138:233-242
Mackic et al. (1998) J. Clin. Invest. 102:734-743
Mackic et al. (2002) Vascular Pharmacol. 18:303-313
Markowski et al. (2000) Neurotoxicol. Teratol. 22:421-428
Matsubara et al. (1999) Ann. Neurol. 45:537-541
Selkoe (1998) Trends. Cell Biol. 8:447-453
Selkoe (2001) Neuron 32:177-180
Shibata et al. (2000) J. Clin. Invest. 106: 1489-1499
Stern et al. (2002) Adv. Drug Delivery Rev. 54:1615-1625
Tanzi et al. (2004) Neuron 43:605-608
Vassar et al. (1999) Science 286:735-741
Walsh et al. (2002) Nature 416:535-539
Yan et al. (1996) Nature 382:685-691
Yan et al. (2000) Nature Med. 6:643-651
Zarcone (2001) J. Neurosci. Meth. 107:107-124
Zlokovic (2005) Trends Neurosci. 28:202-208
Zlokovic et al. (1996) Proc. Natl. Acad. Sci. USA 93:4229-4234

Patents, patent applications, books, and other publications cited herein are incorporated by reference in their entirety.

The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim which recites "comprising" allows inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for deter-mining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method of inhibiting specific receptor-ligand interaction between Alzheimer's amyloid-β peptide (Aβ) and Receptor for Advanced Glycation Endproducts (RAGE) or RAGE activation, comprising administering an effective amount of one or more tertiary amides such that at least some Aβ/RAGE interaction is inhibited; wherein the tertiary amide (s) is selected from the group consisting of FPS1 (3-chloro-N-[2-cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl)-propanamide); FPS2 (3,5-dinitro-N-phenyl-N-[3-[(3,5,5-trimethyl-1-oxohexyl)amino]propyl]-(9Cl)-benzamide); FPS3 (4-chloro-N-[2-(1H-indo-3-yl)-ethyl]-3-nitro-N-(2-pentyl-3-phenyl-allyl)-benzamide); N1A2B1 (N-benzyl-4-chloro-N-cyclohexyl-benzamide); N1A2B2 (N-benzyl-2,4-dichloro-N-cyclohexyl-benzamide); N2A1B1 (4-chloro-N-(3-methyl-butyl)-N-phenethyl-benzamide); N2A2B2 (N-benzyl-2,4-dichloro-N-(3-methyl-butyl)-benzamide); N2A2B3 (N-benzyl-N-(3-methyl-butyl)-3,5-dinitro-benzamide); N2A2B4 (N-benzyl-N-(3-methyl-butyl)-3-nitro-benzamide); N2A2B5 (N-benzyl-4-chloro-N-(3-methyl-butyl)-3-nitro-benzamide); N3A2B2 (N-benzyl-2,4-dichloro-N-(1-ethyl-propyl)-benzamide); N3A2B3 (N-benzyl-N-(1-ethyl-propyl)-3,5-dinitro-benzamide); N3A2B5 (N-benzyl-4-chloro-N-(1-ethyl-propyl)-3-nitro-benzamide); N4A2B2 (N-benzyl-2,4-dichloro-N-(3-phenyl-propyl)-benzamide); and N4A2B5 (N-benzyl-4-chloro-3-nitro-N-(3-phenyl-propyl)-benzamide.

2. A method of inhibiting specific receptor-ligand interaction between Alzheimer's amyloid-β peptide (Aβ) and Receptor for Advanced Glycation Endproducts (RAGE), comprising administering in vivo an effective amount of a tertiary amide to a subject in need of treatment such that Aβ/RAGE interaction is inhibited, wherein the tertiary amide (s) is selected from the group consisting of FPS1 (3-chloro-N-[2-cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl)-propanamide); FPS2 (3,5-dinitro-N-phenyl-N-[3-(3,5,5-trimethyl-1-oxohexyl)amino]propyl]-(9Cl)-benzamide); FPS3 (4-chloro-N-[2-(1H-indo-3-yl)-ethyl]-3-nitro-N-(2-pentyl-3-phenyl-allyl)-benzamide); N1A2B1 (N-benzyl-4-chloro-N-cyclohexyl-benzamide); N1A2B2 (N-benzyl-2,4-dichloro-N-cyclohexyl-benzamide); N2A1B1 (4-chloro-N-(3-methyl-butyl)-N-phenethyl-benzamide); N2A2B2 (N-benzyl-2,4-dichloro-N -(3-methyl-butyl)-benzamide); N2A2B3 (N-benzyl-N-(3-methyl-butyl)-3,5-dinitro-benzamide); N2A2B4 (N-benzyl-N-(3-methyl-butyl)-3-nitro-benzamide); N2A2B5 (N-benzyl-4-chloro-N-(3-methyl-butyl)-3-nitro-benzamide); N3A2B2 (N-benzyl-2,4-dichloro-N-(1-ethyl-propyl)-benzamide); N3A2B3 (N-benzyl-N-(1-ethyl-propyl)-3,5-dinitro-benzamide); N3A2B5 (N-benzyl-4-chloro-N-(1-ethyl-propyl)-3-nitro-benzamide); N4A2B2 (N-benzyl-2,4-dichloro-N-(3-phenyl-propyl)-benzamide); and N4A2B5 (N-benzyl-4-chloro-3-nitro-N-(3-phenyl-propyl)-benzamide.

3. The method according to claim 2, wherein at least some RAGE-mediated Aβ transport into the subject's brain is inhibited by treatment.

4. The method according to claim 2, wherein at least some RAGE activation by Aβ at the subject's blood-brain barrier is inhibited by treatment.

5. The method according to claim 2, wherein at least Aβ is decreased in its amount or concentration in the subject's brain by treatment.

6. The method according to claim 5, wherein at least neuropathology associated with Alzheimer's disease is reduced in the subject's brain by treatment.

7. The method according to claim 2, wherein at least cerebral blood flow is increased in the subject by treatment.

8. The method according to claim 2, wherein memory and/or learning is improved in the subject by treatment.

9. The method according to claim 2, wherein at least some Aβ-RAGE interaction at the subject's blood-brain barrier is disrupted.

10. A method of inhibiting specific receptor-ligand interaction between Alzheimer's amyloid-β peptide (Aβ) and Receptor for Advanced Glycation Endproducts (RAGE), comprising administering in vivo an effective amount of a compound to a subject such that Aβ/RAGE interaction is inhibited, wherein the compound is selected from the group consisting of FPS1 (3-chloro-N-[2-[cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl)-propanamide); FPS2 (3,5-dinitro-N-phenyl-N-[3-[(3,5,5-trimethyl-1-oxohexyl)amino]propyl]-(9Cl)-benzamide); FPS3 (4-chloro-N-[2-(1H-indo-3-y1)-ethyl]-3-nitro-N-(2-pentyl-3-phenyl-allyl)-benzamide); N1A2B1 (N-benzyl-4-chloro-N-cyclohexyl-benzamide); N1A2B2 (N-benzy-2,4-dichloro-N-cyclohexyl-benzamide); N2A1B1 (4-chlor-N-(3-methyl-butyl)-N-phenethyl-benzamide); N2A2B2 (N-benzyl-2,4-dichloro-N-(3-methyl -butyl) -benzamide); N2A2B3 (N-benzyl-N-(3-methyl-butyl)-3,5-dinitro -benzamide); N2A2B4 (N-benzyl-N-(3-methyl-butyl)-3-nitro-benzamide); N2A2B5 (N- benzyl-4-chloro-N-(3-methyl-butyl)-3-nitro-benzamide); N3A2B2 (N-benzyl-2,4-dichloro-N-(1-ethyl-propyl)-benzamide); N3A2B3 (N-benzyl-N-(1-ethyl-propyl)-3,5-dinitro-benzamide); N3A2B5 (N-benzyl-4-chloro-N-(1-ethyl-propyl)-3-nitro-benzamide); N4A2B2 (N-benzyl-2,4-dichloro-N-(3-phenyl-propyl)-benzamide); and N4A2B5 (N-benzyl-4-chloro-3-nitro-N-(3-phenyl -propyl)-benzamide).

11. The method according to claim 10, wherein the compound is N1A2B1 (N-benzyl-4-chloro-N-cyclohexyl-benzamide) or N1A2B2 (N-benzyl-2,4-dichloro-N-cyclohexyl-benzamide).

12. The method according to claim 10, wherein the compound is FPS1 (3-chloro-N-[2-[cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl) -propanamide); FPS2 (3,5-dinitro-N-phenyl-N-[3-[(3,5,5-trimethyl-1-oxohexyl)amino]propyl]-(9Cl)-benzamide); or FPS3 (4-chloro-N-[2-(1H-indo-3-yl)-ethyl]-3-nitro-N-(2-pentyl-3-phenyl-allyl)-benzamide).

13. The method according to claim 1, wherein the tertiary amide(s) is N1A2B1 (N-benzyl-4-chloro-N-cyclohexyl-benzamide) or N1A2B2 (N-benzyl-2,4-dichloro-N-cyclohexyl-benzamide).

14. The method according to claim 1, wherein the tertiary amide(s) is FPS1 (3chloro-N[2-[cyclohexyl[[1-[(4-fluorophenyl)methyl]-1H-pyrrol-2-yl]methyl]amino]-2-oxoethyl]-N-(3-ethoxypropyl)-2,2-dimethyl-(9Cl-propanamide); FPS2 (3,5-dinitro-N-phenyl-N-[3-[(3,5,5-trimethyl-1-oxohexyl)amino]propyl]-(9Cl)-benzamide); or FPS3 (4-chloro-N-[2-(1H-indo-3-yl)-ethyl]-3-nitro-N -(2-pentyl-3-phenyl-allyl)-benzamide).

\* \* \* \* \*